(12) United States Patent
Dhadwal

(10) Patent No.: US 9,474,576 B2
(45) Date of Patent: Oct. 25, 2016

(54) COHERENT IMAGING FIBER BASED HAIR REMOVAL DEVICE

(75) Inventor: Harbans S. Dhadwal, Setauket, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 2408 days.

(21) Appl. No.: 12/246,097

(22) Filed: Oct. 6, 2008

(65) Prior Publication Data

US 2009/0099559 A1  Apr. 16, 2009

Related U.S. Application Data

(60) Provisional application No. 60/977,851, filed on Oct. 5, 2007.

(51) Int. Cl.
  *A61B 18/22* (2006.01)
  *A61B 18/20* (2006.01)
  *A61B 18/00* (2006.01)

(52) U.S. Cl.
  CPC .... *A61B 18/203* (2013.01); *A61B 2018/00452* (2013.01); *A61B 2018/00476* (2013.01)

(58) Field of Classification Search
  CPC .......... A61B 2018/00452; A61B 2018/00476; A61B 18/203; A61B 18/22; A61B 18/20
  See application file for complete search history.

(56) References Cited

U.S. PATENT DOCUMENTS

| | | | |
|---|---|---|---|
| 4,813,412 A | 3/1989 | Yamazaki | |
| 5,425,728 A | 6/1995 | Tankovich | |
| 5,628,744 A | 5/1997 | Coleman | |
| 5,630,811 A | 5/1997 | Miller | |
| 5,653,706 A | 8/1997 | Zavislan | |
| 5,766,214 A | 6/1998 | Mehl | |
| 5,820,625 A | 10/1998 | Izawa | |
| 5,853,407 A | 12/1998 | Miller | |
| 5,860,967 A | 1/1999 | Zavision | |
| 5,870,216 A * | 2/1999 | Brock et al. | 398/49 |
| 5,909,525 A * | 6/1999 | Miller et al. | 385/73 |
| 5,968,033 A | 10/1999 | Fuller | |
| 5,968,034 A | 10/1999 | Fullmer | |
| 6,045,548 A | 4/2000 | Furumoto | |

(Continued)

OTHER PUBLICATIONS

Calum MacAulay et al. "In vivo pathology: microendoscopy as a new endoscopic imaging modality" Gastrointest Endoscopy Clin N Am, 14 (2004) 595-620.*

(Continued)

*Primary Examiner* — Gary Jackson
*Assistant Examiner* — Scott T Luan
(74) *Attorney, Agent, or Firm* — The Farrell Law Firm, P.C.

(57) ABSTRACT

A photoepilation device including a compact hand piece applicator and a portable electronics module for use in a non-medical setting. The hand piece, which contains no electrical signals, allows the user to focus on individual hair follicles by observing a magnified image provided on a semiconductor display. The image from the hand piece is transported to a remote CCD through a coherent imaging fiber. which also delivers the therapeutic energy pulse from a remotely located source to the localized target. Destruction of pluripotential follicular stems cells found in the hair bulb and bulge regions is possible via a single low power laser diode. Control of pulse width and spot size attains a range of fluence levels up to 85 J·cm$^{-2}$.

5 Claims, 9 Drawing Sheets

(56) References Cited

U.S. PATENT DOCUMENTS

| | | | |
|---|---|---|---|
| 6,059,777 A | 5/2000 | Acquaire | |
| 6,110,195 A | 8/2000 | Xie | |
| 6,149,644 A | 11/2000 | Xie | |
| 6,149,645 A | 11/2000 | Tobinick | |
| 6,162,212 A | 12/2000 | Kreindel | |
| 6,165,171 A | 12/2000 | Tobinick | |
| 6,168,589 B1 | 1/2001 | Tobinick | |
| 6,168,590 B1 | 1/2001 | Neev | |
| 6,200,308 B1* | 3/2001 | Pope et al. | 606/9 |
| 6,217,572 B1 | 4/2001 | Tobinick | |
| 6,228,075 B1 | 5/2001 | Furumoto | |
| 6,235,015 B1 | 5/2001 | Mead | |
| 6,254,596 B1 | 7/2001 | Lawandy | |
| 6,267,771 B1 | 7/2001 | Tankovich | |
| 6,273,884 B1 | 8/2001 | Altshuler | |
| 6,273,885 B1 | 8/2001 | Koop | |
| 6,383,176 B1 | 5/2002 | Connors | |
| 6,485,484 B1 | 11/2002 | Connors | |
| 6,511,475 B1 | 1/2003 | Altshuler | |
| 6,517,532 B1 | 2/2003 | Altshuler | |
| 6,537,270 B1 | 3/2003 | Elbrecht | |
| 6,569,155 B1 | 5/2003 | Connors | |
| 6,569,156 B1 | 5/2003 | Tankovich | |
| 6,579,283 B1 | 6/2003 | Tobinick | |
| 6,595,985 B1 | 7/2003 | Tobinick | |
| 6,641,578 B2 | 11/2003 | Mukai | |
| 6,663,620 B2 | 12/2003 | Altshuler | |
| 6,682,524 B1 | 1/2004 | Elbrecht | |
| 6,723,090 B2 | 4/2004 | Altshuler | |
| 6,970,615 B1* | 11/2005 | Fang et al. | 385/16 |
| 6,976,985 B2 | 12/2005 | Altshuler | |
| 7,063,694 B2 | 6/2006 | Nahen | |
| 7,101,365 B1 | 9/2006 | Sharon | |
| 7,118,563 B2 | 10/2006 | Weckwerth | |
| 7,123,636 B2 | 10/2006 | Yamazaki | |
| 7,136,405 B2 | 11/2006 | Yamazaki | |
| 7,214,222 B2 | 5/2007 | Yamazaki | |
| 7,220,254 B2 | 5/2007 | Altshuler | |
| 7,254,429 B2 | 8/2007 | Schurman | |
| 7,263,255 B2 | 8/2007 | Anderson | |
| 2002/0091377 A1 | 7/2002 | Altshuler | |
| 2003/0045916 A1* | 3/2003 | Anderson et al. | 607/89 |
| 2003/0233138 A1 | 12/2003 | Spooner | |
| 2004/0167499 A1 | 8/2004 | Grove | |
| 2004/0167500 A1 | 8/2004 | Weckwerth | |
| 2004/0260210 A1 | 12/2004 | Ella | |
| 2005/0124984 A1 | 6/2005 | Wagnleres | |
| 2005/0154382 A1* | 7/2005 | Altshuler et al. | 606/9 |
| 2005/0215988 A1 | 9/2005 | Altshuler | |
| 2005/0267457 A1 | 12/2005 | Hruschka | |
| 2006/0116669 A1 | 6/2006 | Dolleris | |
| 2007/0016176 A1* | 1/2007 | Boutoussov et al. | 606/17 |
| 2007/0032781 A1 | 2/2007 | Henry | |
| 2007/0032847 A1 | 2/2007 | Weckwerth | |
| 2007/0198004 A1 | 8/2007 | Altshuler | |

OTHER PUBLICATIONS

G.B. Altschuler et al, "Extended theory of selective photothermolysis," Lasers in Surgery and Medicine, 29: 416-432 (2001).

SP Amin and DJ Goldberg, "Clinical comparison of four hair removal and light sources," J. Cosmetic and Laser Therapy, 8: 65-68 (2006).

X.J. Wang et al, "Characterization of human scalp hairs by optical low-coherence reflectometry," Opt. Let., 20, 6, 524-526 (1995).

R.M. Porter et al, "Functional analysis of keratin components in the mouse hair follicle inner root sheath," Brit. J. Dermatology, 150, 195-204 (2004).

L. Langbein et al, "K6irsl, K6irs2, K6irs3 and K6irs4 Represents the inner root sheath specific type II epithelial keratins of the human hair follicle," J. Invest. Dermat., 120 512-522 (2003).

* cited by examiner

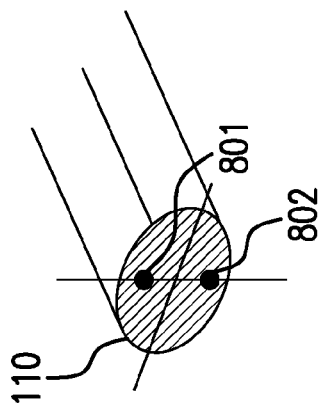
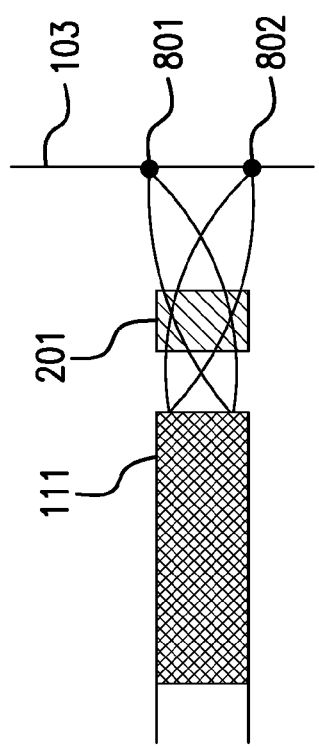
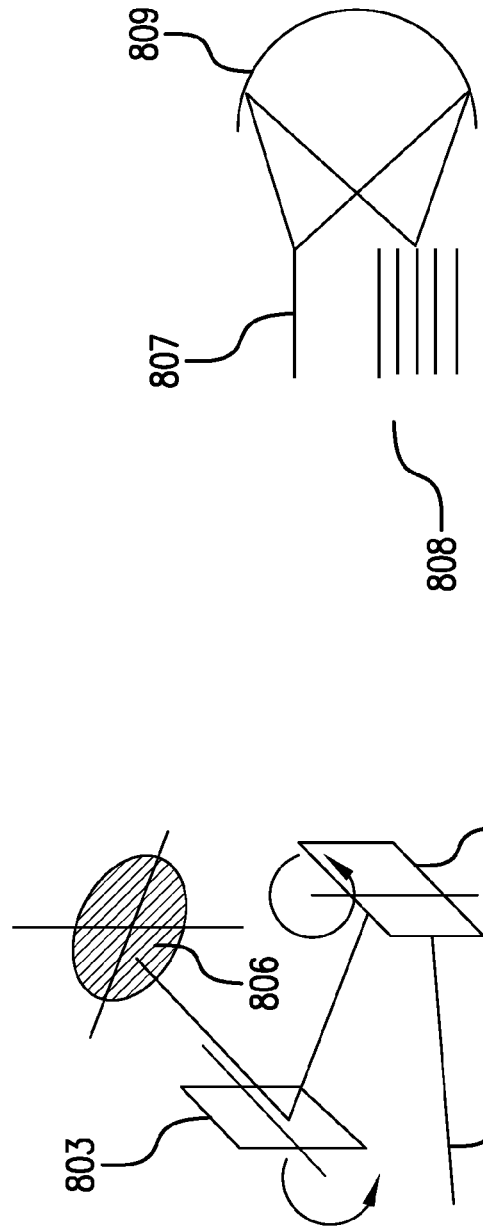

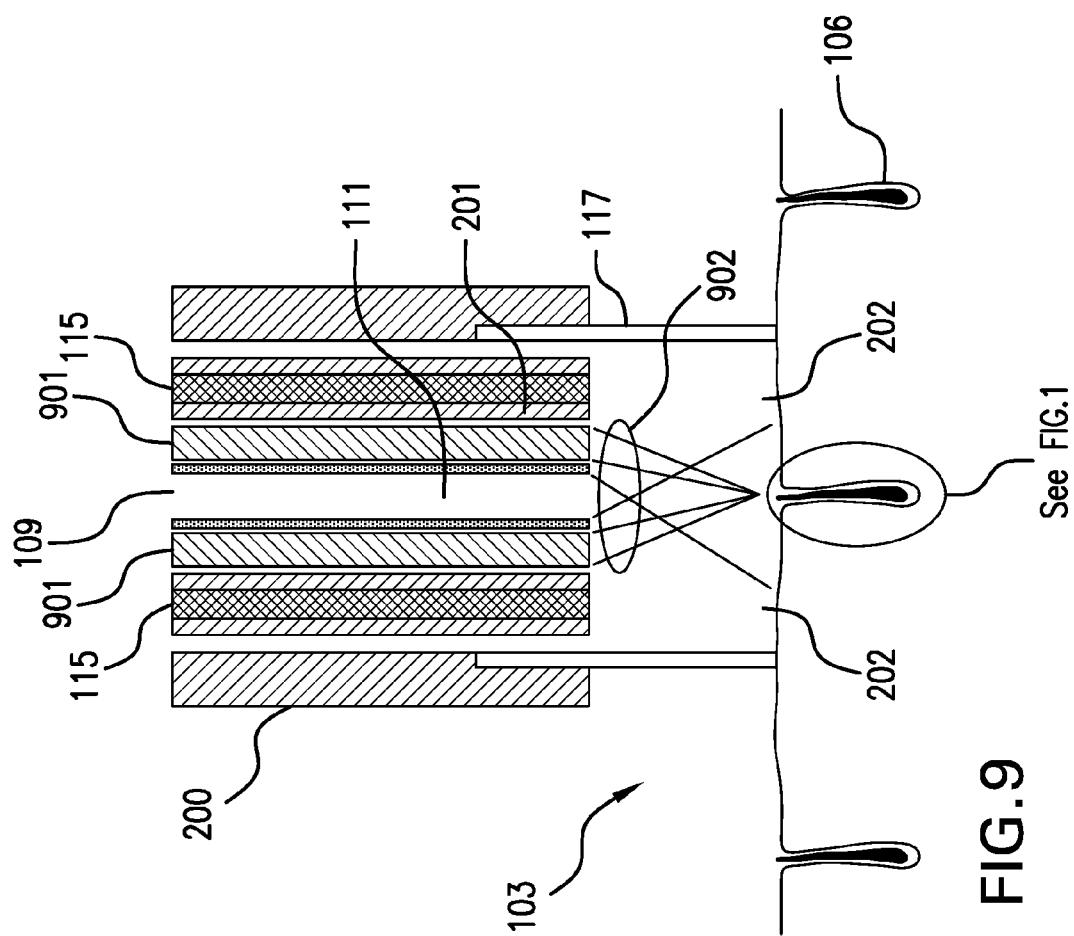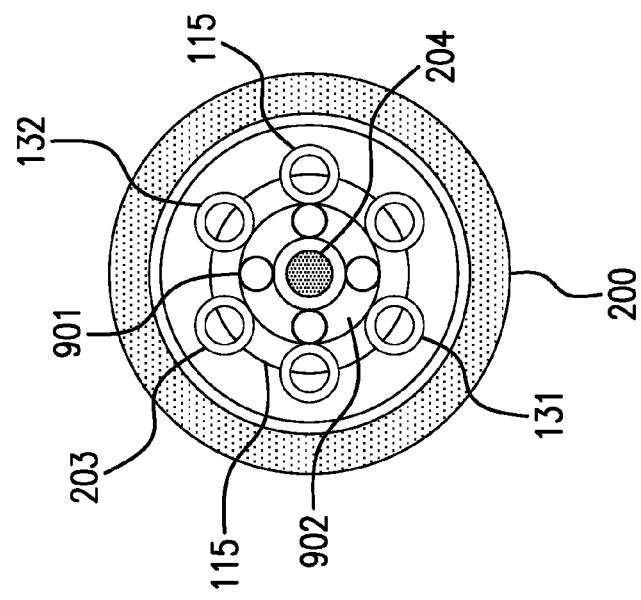
FIG. 9

COHERENT IMAGING FIBER BASED HAIR REMOVAL DEVICE

PRIORITY

This application claims priority to U.S. Provisional Application No. 60/977,851, filed Oct. 5, 2007, the content of which is incorporated herein by reference.

BACKGROUND OF THE INVENTION

1. Field of the Invention

The present invention relates generally to selective and extended photothermolysis for cosmetic, health and dermatology conditions, and more particularly, to a portable device for photo-inducing damage to cellular structures for hair removal.

2. Brief Description of the Background Art

Electromagnetic energy, particularly in the optical band of 400 nm to 1200 nm, has been used for treatment of many skin related diseases as well as for cosmetic procedures, such as, hair removal, spider veins, tattoos, port wine stains, skin rejuvenation and photodynamic therapy. Laser and light-based removal of hair, both in men and women, is widely accepted as a successful approach. In today's market place, manufacturers have focused on four laser-based systems: 1) alexandrite (755 nm); 2) neodymium-doped yttrium aluminum garnet (1064 nm); 3) laser diodes (810 nm); and 4) a broad band Intense Pulsed Light (IPL) source. Generally, these systems provide reduction in the growth cycle of removed hair. Multiple treatments have been found to improve upon longevity of the hair free period. An endpoint for an acceptable treatment requires destruction of pluripotential follicular stem cells and not merely evaporation of the hair shaft.

Recent data suggests that the stem cells are found in upper bulb and bulge regions of the hair follicle. Indeed there may be other areas not yet identified. Laser Hair Removal (LHR) procedures must target these regions of the stem cells, as they are responsible for hair growth. Several techniques have been developed for destruction of stem cells.

Laser ablation, not typically used for photoepilation, uses high energy short pulses to raise the temperature of the stem cell above that required for evaporation, however, the target and the absorber must be collocated. Selective Photothermolysis (SP) exploits dissimilar absorption coefficients of the photo absorbers and surrounding tissue. However, use of SP for destroying the stem cells responsible for hair growth is compounded because the photo-absorbing chromophore, melanin, is found both in the follicular stem cells and the epidermis. Melanin has a broad absorption spectrum and is responsible for pigmentation of the hair shaft and skin. SP techniques are effective if a concentration of melanin is higher, by a factor of five, in the target area. These techniques work particularly well for dark hair on light skin. However, unavoidable absorption of photons in the epidermis leads to heat, which needs to be removed to avoid damage to the epidermis. Consequently, innovative handpieces which chill the epidermis during treatment have been developed.

Destruction of cells through thermal denaturing requires that a target temperature exceeding 70° C. within the Thermal Relaxation Time (TRT) of the tissue. For the hair shaft, the TRT is in the range of 35 to 50 ms. Pulse widths exceeding the TRT permit diffusion of heat into surrounding tissue preventing the denaturing temperature from being reached due to heat leakage. Typically, LHR devices target about a ~1 cm² area of the skin, which is bombarded with photons. Some photons are absorbed in the epidermis, while the remaining migrate, via scattering, through the dermis and reach the melanin rich hair shaft and bulb region, where absorption leads to elevation of tissue temperature causing cell destruction. The photons scattered in the backward direction return back to the epidermis resulting in fluence levels exceeding the incident fluence.

Based on photon transport theory and clinical data, an optimum set of parameters can be established for a particular device. Unfortunately, these parameters are patient dependent and use of LHR devices remains an art.

A typical laser diode system will have a variable fluence between 20 to 60 $J \cdot cm^{-2}$, a pulse width in the range of 5 to 500 ms, and a treatment spot size of ~1 cm². The peak power of the source, which determines the size of the LHR system, is proportional to the product of fluence and spot area and inversely proportional to the pulse width. For example, a 100 μs pulse with a spot area of 1 cm² requires a peak pulse power of 20 kW for a fluence of 20 $J \cdot cm^2$. Consequently, this leads to bulky and expensive machines, which need full medical facilities for operation. While the large diameter reduces treatment time and increases penetration depth into the dermis, it lacks the capability to selectively remove hair from a given area, i.e. to reduce hair density.

Another approach for permanent hair removal is based on Extended Selective Photothermolysis (ESP). The target to be denatured can be separated from a photo-absorber, known as a heat source. A closer study of the underlying thermal diffusive processes has led to use of longer pulses to produce a hot spot in the melanin rich hair shaft. The longer laser pulse produces a hot spot, which begins to heat the surrounding tissue, including the hair bulb and bulge. Pulse width is determined by the TRT and the Thermal Damage Time (TDT). Recent studies have indicated, particularly for techniques using the hair shaft for heat transmission, that a longer pulse width up to 1.5 s may be acceptable, which substantially decreases the peak power requirement. Several LHR systems with peak power up to 200 W using laser diode arrays are now on the market.

Other procedures for efficiently using the available photons in LHR devices include the use of highly reflective and thermally conductive applications to the skin prior to laser treatment. Ultrasonic massaging increases penetration of a dye into the epidermis. Pre-treatments can be used with any of the light-based techniques to enhance efficacy of hair removal, but adds extra time and cost to the treatment.

U.S. Pat. No. 7,118,563 to Weckwerth, the disclosure of which is incorporated herein by reference, discloses a rechargeable device suitable for providing therapeutic energy. However, the minimum spot size of 0.25 cm² is too large for targeting single hair follicles and causes a reduction in the peak power requirement. The system disclosed by Weckwerth also lacks any imaging device for identifying a treatment area.

U.S. Pat. No. 7,220,254 to Altshchuler, the disclosure of which is incorporated herein by reference, teaches that existing technology can be packaged into a self-contained hand-held device for delivery of therapeutic energy to a skin treatment area and can be visualized by an image capturing system integrated into the hand-held device. The device combines discrete optical and electronic components to illuminate an area of the skin to facilitate imaging by a Charge Coupled Device/Complementary Metal Oxide Semiconductor (CCD/CMOS) device. Imaging and treatment optical paths are separated by a beam splitter. A more compact and user-friendly hand-held device, with few components, would be more desirable, particularly for the home market.

In fact, in keeping with this concept, U.S. Pub. No. 2007/0198004 Altschuler et al., the disclosure of which is incorporated herein by reference, addresses some of the above problems in disclosing a tethered hand-piece which may be more appropriate for the home market. However, conventional photo cosmetic devices do not include imaging capability and use lower power EMR sources having prolonged exposure times. For hair removal, such devices recommend power levels in the range of 20-500 W, which is not attainable by a single laser diode.

SUMMARY OF THE INVENTION

The present invention discloses a compact hand piece applicator for LHR, including a Coherent Imaging Fiber (CIF); a fiber optic ON/OFF switch; optical fibers for white light illumination; a chilled air delivery system; imaging optics; and an extender for scanning a treatment spot. The CIF serves a dual purpose. The CIF: 1) provides an image of a target area, for example, a hair follicle; and 2) delivers therapeutic energy from a remote optical source to the target area. The spatial cross-sectional distribution of the therapeutic laser energy can be shaped by exciting appropriate pixels in the CIF, for example, a circular spot or a donut shaped spot. The hand-piece provides the ability to alter a size of the target area, which is generally smaller than a diameter of the hair follicle. A Laser Diode (LD) having a wavelength in the range 750 to 850 nm, provides a broad range of pulse widths applicable to SP or ESP. A power level of the optical source can be increased through use of multiple single LDs or a single laser diode array. The fiber optic switch, which can be replaced by an optical microphone, initiates the delivery of the laser diode energy pulse or pulses. Absence of electrical signals in the hand piece offers added safety to a home user. Further the invention includes a portable electronic system, which provides all controls necessary to operate the system and to interface with other computing devices.

BRIEF DESCRIPTION OF THE DRAWINGS

The above and other objects, features and advantages of certain embodiments of the present invention will be more apparent from the following detailed description taken in conjunction with the accompanying drawings, in which:

FIG. 8 provides schematics for producing a scanning spot on a target, according to an embodiment of the present invention; and FIG. 9 is a schematic of the fiber optic hand piece applicator, according to an embodiment of the present invention.

DETAILED DESCRIPTION OF THE PREFERRED EMBODIMENTS

The following detailed description of preferred embodiments of the invention will be made in reference to the accompanying drawings. In describing the invention, explanation about related functions or constructions known in the art are omitted for the sake of clearness in understanding the concept of the invention, to avoid obscuring the invention with unnecessary detail.

Embodiments of the present invention provide a portable and inexpensive apparatus for locating and capturing an image of a small treatment area, typically, about 250 microns in diameter. Further, the apparatus, typically less than 15 mm in diameter, delivers optical energy from a remote source to a target area, preferably smaller than a size of the image. The small size the apparatus is particularly useful for treatment areas that require a reduction of hair density and not indiscriminate hair removal. In a preferred embodiment, the apparatus includes a hand piece mounted on a robotic arm for automated laser hair removal.

Figure 1:
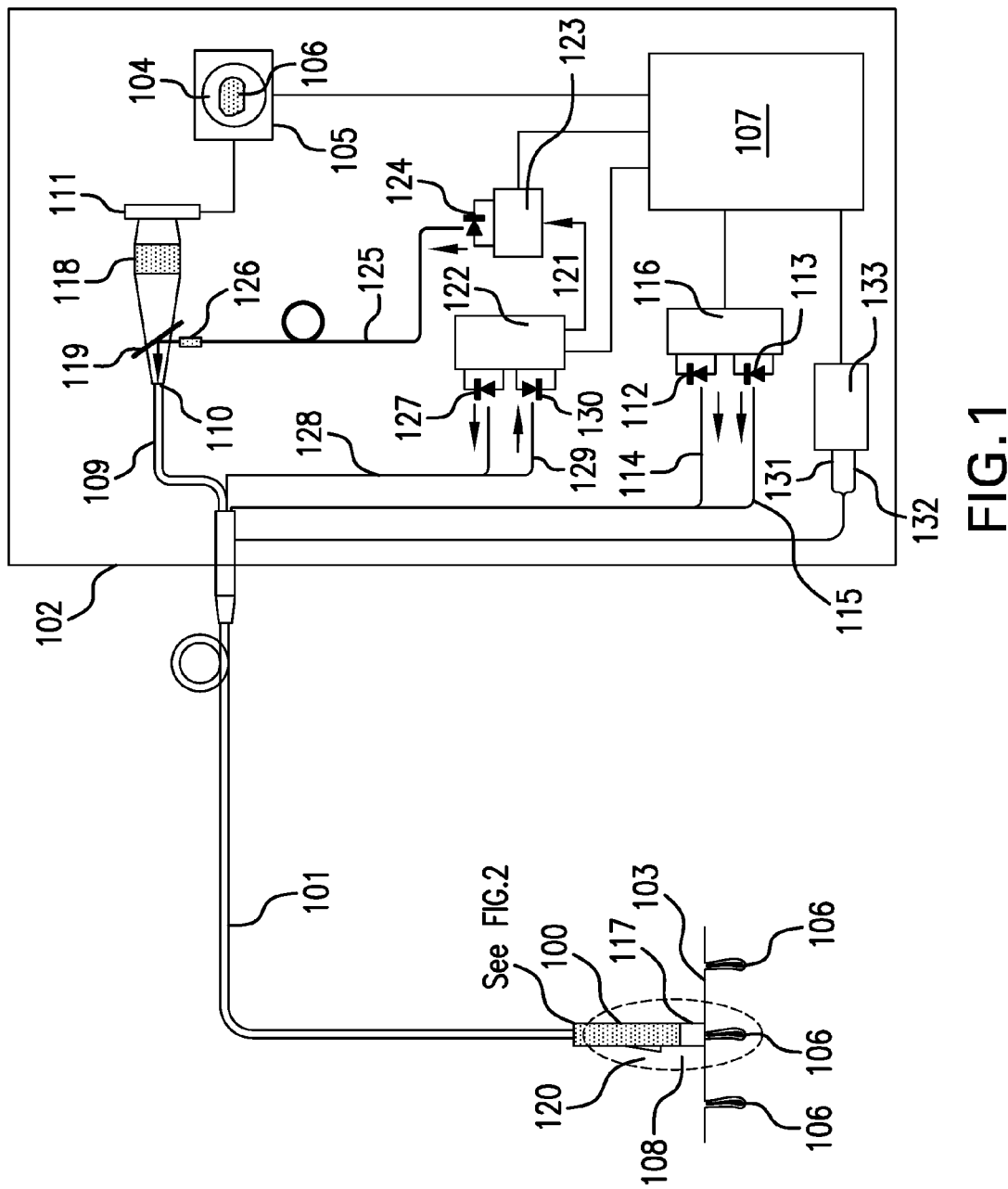
FIG. 1 is a block diagram of a portable laser hair removal system, according to an embodiment of the present invention.
Figure 2:
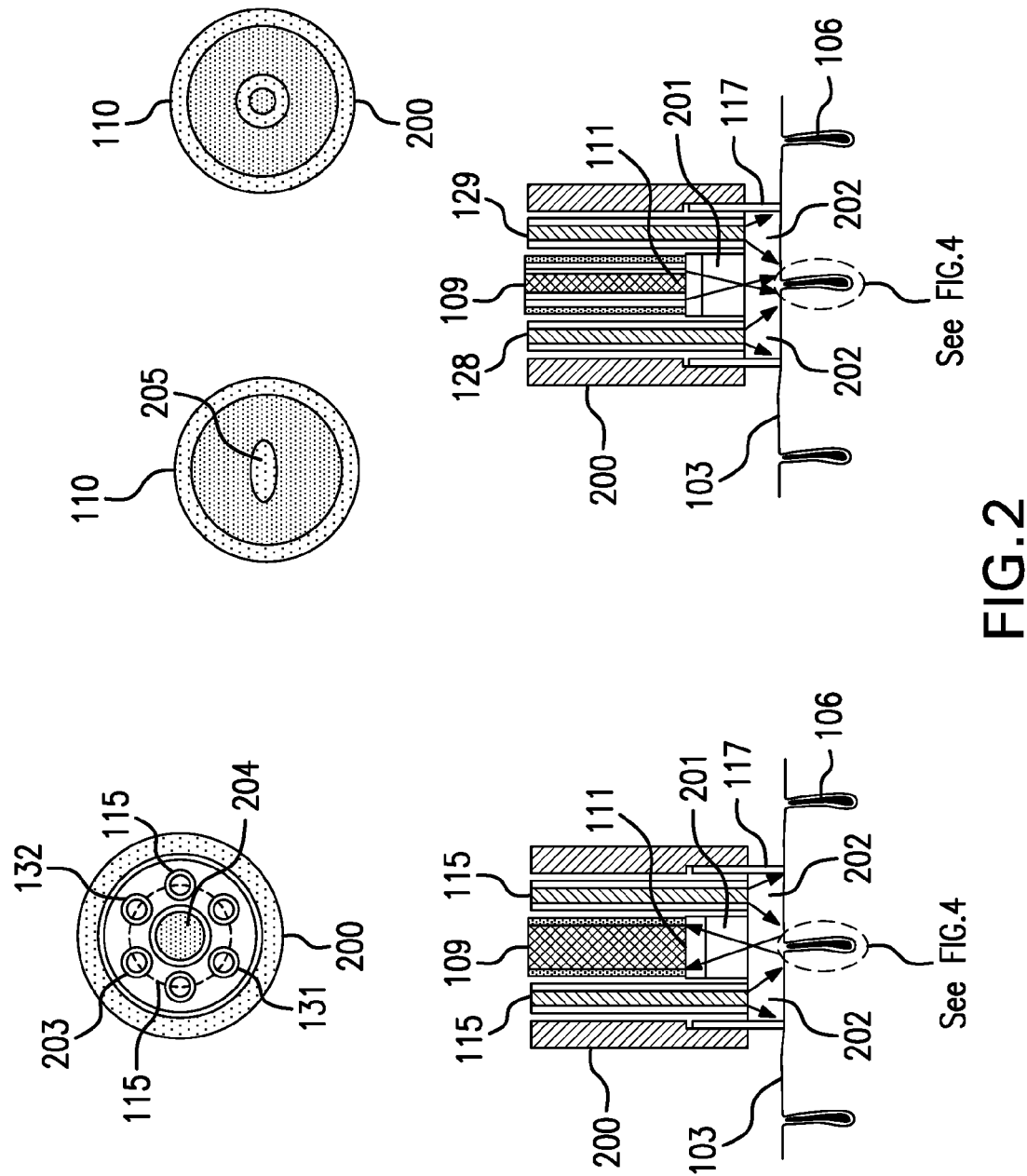
FIG. 2 is a schematic of a fiber optic hand piece applicator of the portable laser hair removal system of FIG. 1, according to an embodiment of the present invention.

Additionally, the small treatment laser spot can be scanned across the target area to synthesize a larger treatment area. Referring to FIG. 1 a miniature Hand Piece Applicator (HPA) 100 is connected to an electronic console 102 by a the flexible umbilical cord 101. The HPA 100 can be operated either in manual mode or as part of a robotic arm for automated treatment. In the manual mode, the HPA 100 is moved along the surface of a treatment area 103, while viewing a color image 104 on a display screen 105, until a particular target 106, for example a hair follicle, is located. At this point the color image 104 can be captured and stored in an embedded processor system 107. Referring to FIG. 2, the image capture system comprises of two optical imaging stages: the first stage uses a microlens 201 to form a primary image 207 of the treatment area 103 at the distal end 109 of the Coherent Imaging Fiber (CIF) 108, which transports the image 207 to CIF's 108 proximal end 110; an aspheric lens 111 forms a magnified image 104 of the CIF's proximal end on to the surface of the CCD/CMOS device 112. Magnification of the primary image 207 is adjustable through a height of opaque baffle 118. A dichroic beam splitter 119 separates low energy visible imaging path from the high laser pulse delivery path.

Illumination of the treatment surface 106 is achieved by coupling an output from white light emitting diodes 113 and 114 to the proximal end of multimode optical fibers 115 and 116, which transport the light to the HPA 100 through the umbilical cord 101. Intensity of illumination is controlled through a ON/OFF optical switch control module 121.

An optical system responsible for delivering a high energy Therapeutic Laser Pulse (TLP) to the target 106 uses the same CIF 109 described above for capturing the image of the target. In the manual mode, transmission of the TLP is initiated by a user command, which is generated by an ON/OFF optical switch 120 mounted in the HPA 100. Upon receiving ON signal from the LED driver assembly, the embedded processor system 107 sends out a programmed series of pulses to a Laser Diode (LD) driver 126, which drives the LD 127, which is pigtailed to a multimode fiber 128, the output from the distal end is imaged to the proximal surface 110 of the CIF 109 via a source imaging aspheric lens 129 and a dichroic mirror 119. The electro-mechanical shutter 133 prevents accidental leakage of the high laser energy, and its operation is synchronized with the ON/OFF pulse. A proximal image of the TLP is transported to the distal end 109 of the CIF 108 in the HPA 100. In this manner, the TLP is delivered precisely to the target 106 with negligible energy leakage beyond the treatment area 103. Pulse parameters are adjustable through the embedded processor system 107.

The optical switch 120, also discussed in regard FIG. 3, modulates an optical signal to define its ON/OFF states. A modulated signal from the control module 121 drives Light Emitting Diode LED 122, which is pigtailed to an optical fiber 125. During the ON state, the modulated optical signal from the HPA 100 is returned back to the control module 121 via an optical fiber 124 which is pigtailed to a photodetector 123, typically, a pin photodiode. The received optical signal is detected and sent to the embedded processor system 107, which uses the ON state to generate the TLP with a preset width and amplitude, and the OFF state is used for shutting down the high power laser diode 127. The ON/OFF signal can be used to provide authentication codes to prevent accidental or unauthorized use of the HPA. The HPA 100 also provides chilled air directed at the treatment area 103. The chilled air is delivered through two stainless steel micro-tubes 131 and 132 from a chilled air source controller 133.

Referring to FIG. 2A, FIG. 2A illustrates a cross-section of the HPA 100 constructed from a cylindrical stainless steel housing 200. For aesthetic purposes, the HPA 100 may be further encased in a specialized molding (not shown). The CIF 108 is located in a central region of the HPA 100, surrounded by a ring containing tubing and optical fibers, as discussed below. The CIF 108 typically has a diameter of 700 microns and 50,000 individual pixel elements each having a diameter of 4.5 microns. The distal end 109 of the CIF 108 is positioned in a front conjugate plane of microlens assembly 201. As illustrated in FIG. 2B, the microlens assembly 201 forms a de-magnified primary image 207 of the target 106 on the distal end 109 of the CIF 108. The primary image is transported to the proximal end 110 as discussed above. The primary image size 207 can be adjusted by changing the height of the baffle 117. Plurality of multimode optical fibers 114 and 115 provide white light illumination 203, to enhance quality of a captured image. The stainless steel micro-tubes 131 and 132 are used for transporting chilled air to the treatment area 103. Stainless steel conduit 203 is used for holding multimode optical fibers 124 and 125 used in the optical switch 120 illustrated in FIG. 3, while spare stainless steel channel 204 may be used for mounting other sensors, for example, a thermistor for monitoring the target temperature.

During the treatment mode, the CIF 108 delivers the optical energy to the target 106. As illustrated in FIG. 2B, it is possible to define any arbitrary spatial distributions 205 and 206 by exciting the appropriate pixels at the proximal end 110 of the CIF 108. The microlens assembly 201 produces the desired spatial image on the target 106. The optical energy is delivered to the treatment area 103 for a programmed precise time and the laser diode 124 is disabled until the optical switch 120 is enabled.

Figure 3B:
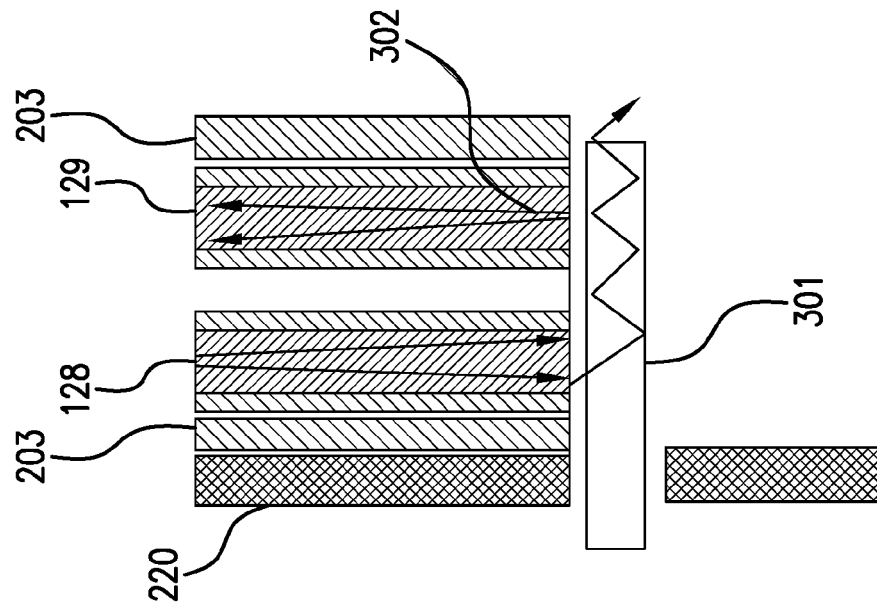
FIG. 3 provides a cross-sectional view of an optical switch of the portable laser hair removal system of FIG. 1, according to an embodiment of the present invention.
Figure 3A:
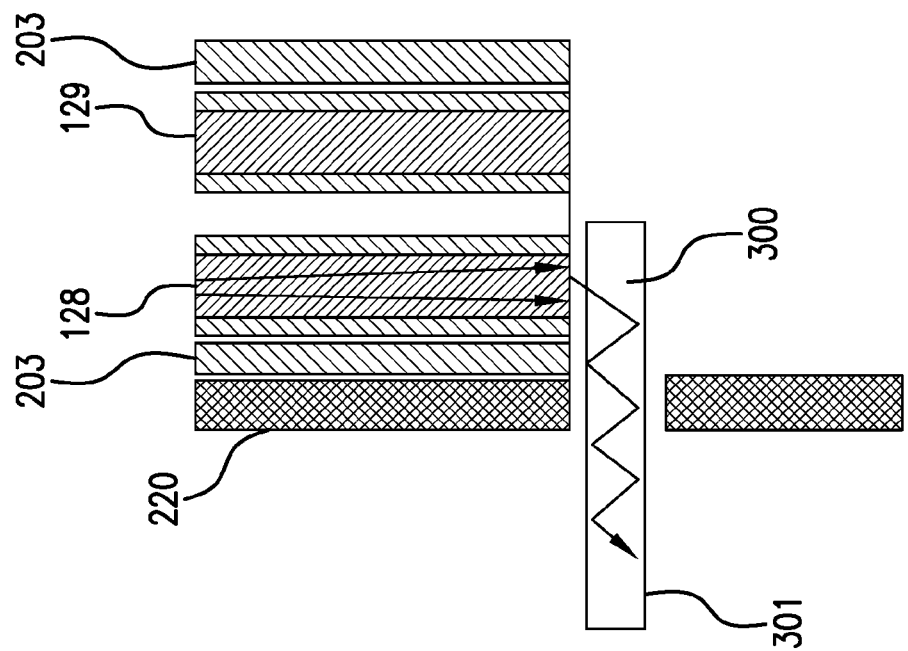

FIG. 3 is illustrates a cross-sectional view of the optical switch 120 in the HPA 100. Two multimode optical fibers 124 and 125 are mounted in the stainless micro-tubing 203. A modulated optical signal emanates from a distal end of fiber 125. In the OFF state, illustrated in FIG. 3A, an optical signal 300 enters a slab waveguide 301 and is lost. In the ON state, as illustrated by FIG. 3B, the optical signal 300 enters the slab waveguide 301, and some of the optical signal leaves the slab waveguide 301, entering the fiber 129. The optical signal is detected by the photodetector 123 in FIG. 1. The optical switch 120 defaults to the OFF state until moved to the ON state by the user. Activation of the optical switch 120 will produce a TLP of preset width and repetition rate. This feature adds another layer of safety.

Figure 4:
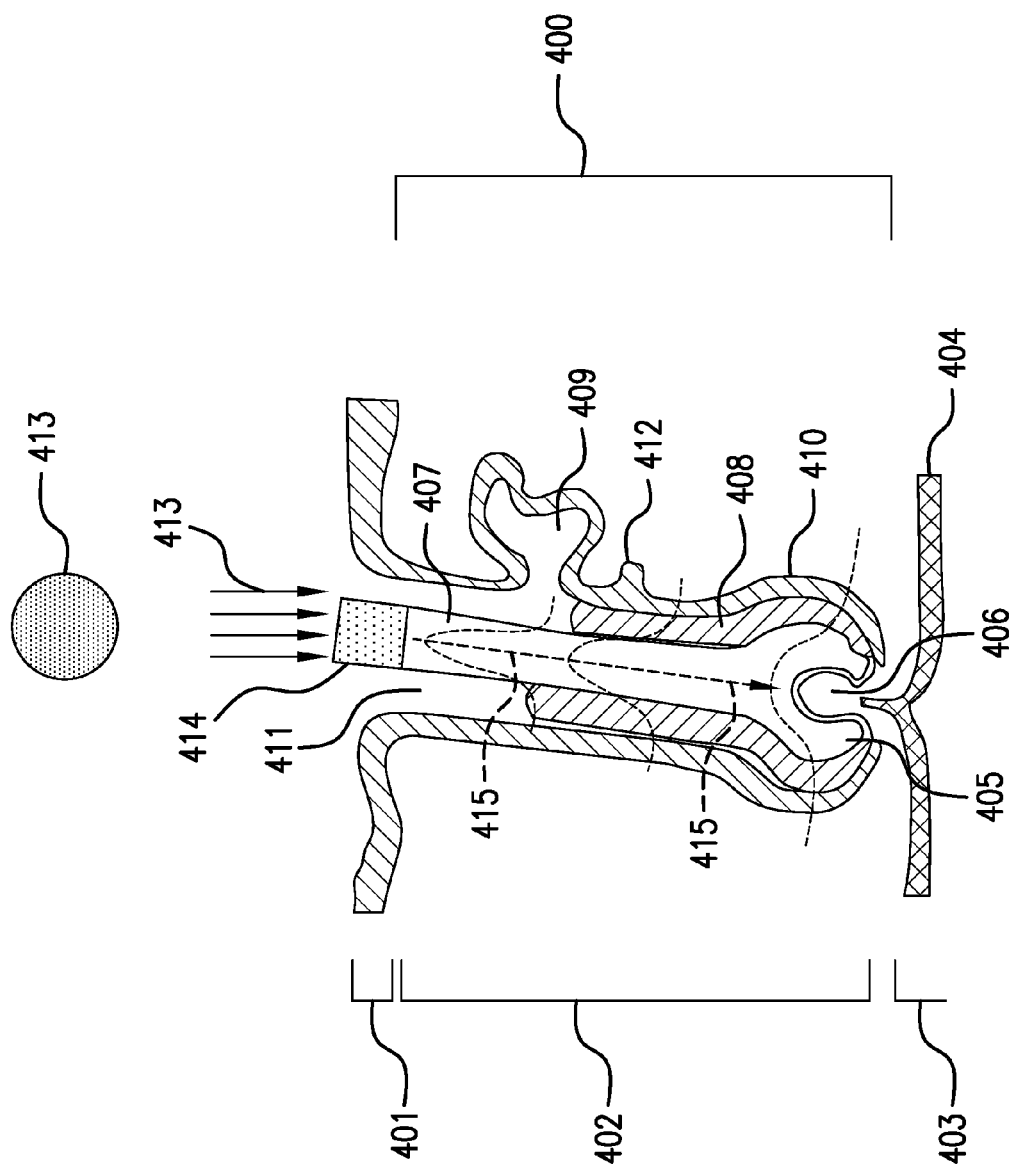
FIG. 4 is a cross-sectional view of a hair follicle with direct illumination of a hair shaft, according to an embodiment of the present invention.

FIG. 4 shows a cross-section of a hair follicle 400, which resides in the following three layers of the skin: 1) the epidermis 401; 2) the dermis 402; and 3) the hypodermis 403. During the anagen phase of the hair growth cycle, capillaries 404 provide nutrients to the bulb region 405, which encompasses the dermal papilla 406. During this phase of the hair growth cycle, the bulb region 405 is located 2 to 4 mm below the epidermis 401. The hair shaft 407 and the Inner Root Sheath (IRS) 408 grow together from the bulb region 405 upward toward the sebaceous gland 409. Each of the various follicular compartments arises from the germinative cell pool at the base of the bulb region 405. An inner most layer of the Outer Root Sheath (ORS) 410 provides a slippage plane. The ORS 410 remains behind and is continuous with the epidermis 401. The IRS 408 disintegrates just below the sebaceous gland 409 and the sheath-free hair shaft 407 exits the pilary canal 411. The bulge region 412, the putative site of follicular stem cells and the bulb region 405 contain melanocytes, which give the hair shaft 407 its color. The bulge region 412 and the bulb region 405 are the primary targets for photothermolysis as they exhibit a broad absorption spectrum in the visible and near infrared regions. Melanocytes are composed of eumalanin, which is brownish-black, and phuemelanin, which is reddish. Photons from the TLP are delivered to the bulge region 412 and the bulb region 405 in order to cause cell destruction. SP methods of photoepilation bombard a large area of the epidermis 401 in order to increase the probability of reaching target areas. Photons in the TLP are lost due to reflection at the epidermis 401, absorption in the epidermis 401, and scattering in the dermis 402. The probability of photons reaching intended targets is extremely low, requiring high surface fluence values and large treatment area sizes. In addition, deeper targets, such as the hair follicle 400, are only reachable at longer wavelength (750-1000 nm). However, the absorption of melanin drops of at longer wavelengths, requiring even higher fluences.

Decreasing a requirement for peak power through a reduced spot size of the TLP pulse is not a viable solution as the photons migrate out of the target zone very rapidly. Moving to a smaller spot size demands new delivery methods for reaching the intended targets. Three optical delivery techniques are provided which target individual hair follicles, typically with a spot size smaller than $10^{-4}$ cm$^2$. One of these is the ESP, which uses heat diffusion to reach the intended targets by creating hot spots in easily accessible parts of the hair follicle, mainly the hair shaft 407. However, delivering the TLP directly to the hair shaft 407, which has a nominal diameter of 80 μm, requires precise spatial location. Imaging and sensor techniques have been proposed for achieving this goal, but all of the proposed solutions include scanning functionality in the hand piece, something that should be avoided if the device is to be utilized in non-medical facilities.

One possible strategy, illustrated in FIG. 4, is to illuminate the hair shaft 407 with a Gaussian laser spot 413, with a diameter slightly smaller than a diameter of the hair shaft 407, typically about of 80 μm and the pilary canal 411 has an opening with a nominal diameter of 200 μm. The hair shaft 407 is a highly absorbing medium and has no useful optical guiding properties. In "Characterization of human scalp hairs by optical low-coherence reflectometry," Opt. Let., 20, 6, 524-526 (1995) by Wang et al., optical low-coherence reflectometry measurements of longitudinal scans of dark and light hair are provided. Wang et al. reported that a refractive index of the hair shaft increased from 1.57 for blond hair to 1.59 for black hair. From the data of Wang et al., an attenuation coefficient for black and blond hair was estimated to be 34.5 $mm^{-1}$ and 3.2 $mm^{-1}$, respectively. From these measurements, made at 850 nm, effective penetration depths of 29 μm and 310 μm for black and blond hair, respectively, was determined. These measurements indicate that the hair shaft is not an optical fiber waveguide. Thus, photons incident on the hair shaft are absorbed within this short layer, causing a localized hot spot 414. By using lower fluences and longer pulse widths (500 ms), the dermal papilla 405 and bulb region 406 can be heated to denaturing temperatures by allowing the heat to diffuse down the hair shaft 407 as indicated by 415.

Figure 5:
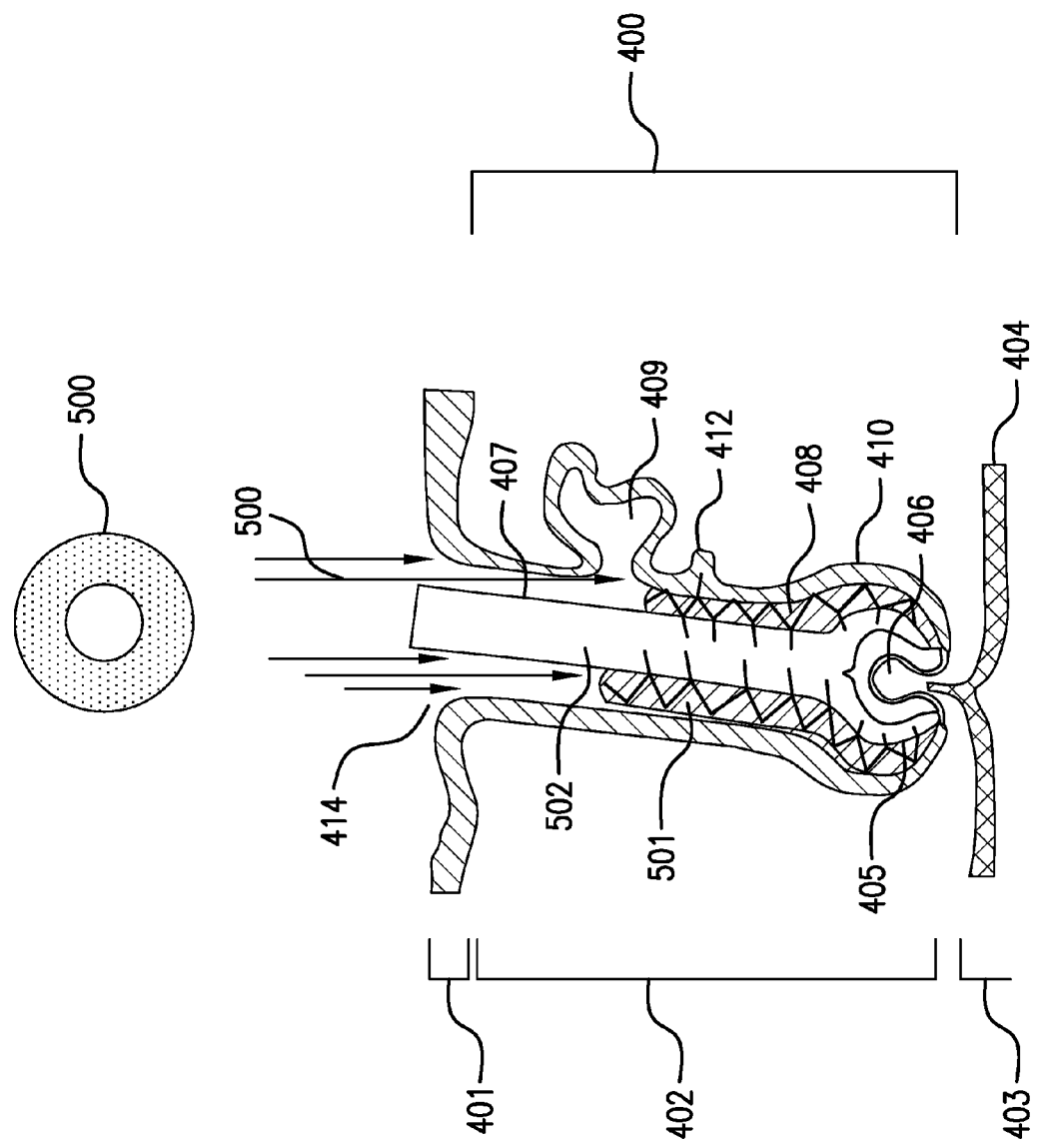
FIG. 5 is a cross-sectional view of the hair follicle with direct illumination of an inner root shaft using a donut beam, according to an embodiment of the present invention.

FIG. 5 shows a second illumination strategy, which deposits photons in melanin rich sites of the hair shaft 407 by using an optical guiding channel created by a concentric structure of the hair shaft 407, the IRS 408, and the ORS 410. Specifically, the hair shaft 407, the IRS 408, and the ORS 410 form a three layer waveguide. Entrance to the three layer waveguide is through the pilary canal 411. The IRS 408, which is sandwiched between the ORS 410 and the hair shaft 407, below the sebaceous gland 409, has a refractive index that is larger than that of the ORS 410 but lower than that of the hair shaft 407. The three layers form a leaky waveguide, with the photons being absorbed on a hair shaft surface 502 and reflected from an ORS surface 501. A donut shaped TLP 500 is matched to a size of the pilary canal 411, which has inner diameter bounded by the hair shaft 407 and a nominal ring thickness 30-40 μm. Photons enter the pilary canal 411, which may contain an oil substance excreted by the sebaceous gland 409, enter the IRS 408 below the sebaceous gland 409, and are guided through the leaky modes to the melanin rich bulb region 405 containing the stem cells to be destroyed. As these photons travel in the IRS 408 some are likely to be absorbed by the melanocytes in the bulge region 412. The fluence levels may be lower as none of the incident photons are absorbed by the epidermis 401 or the dermis 402. Consequently the epidermis 401 should experience minimum heat stress. In this configuration pulse widths should correspond to the TRT of the bulb region 405.

Figure 6:
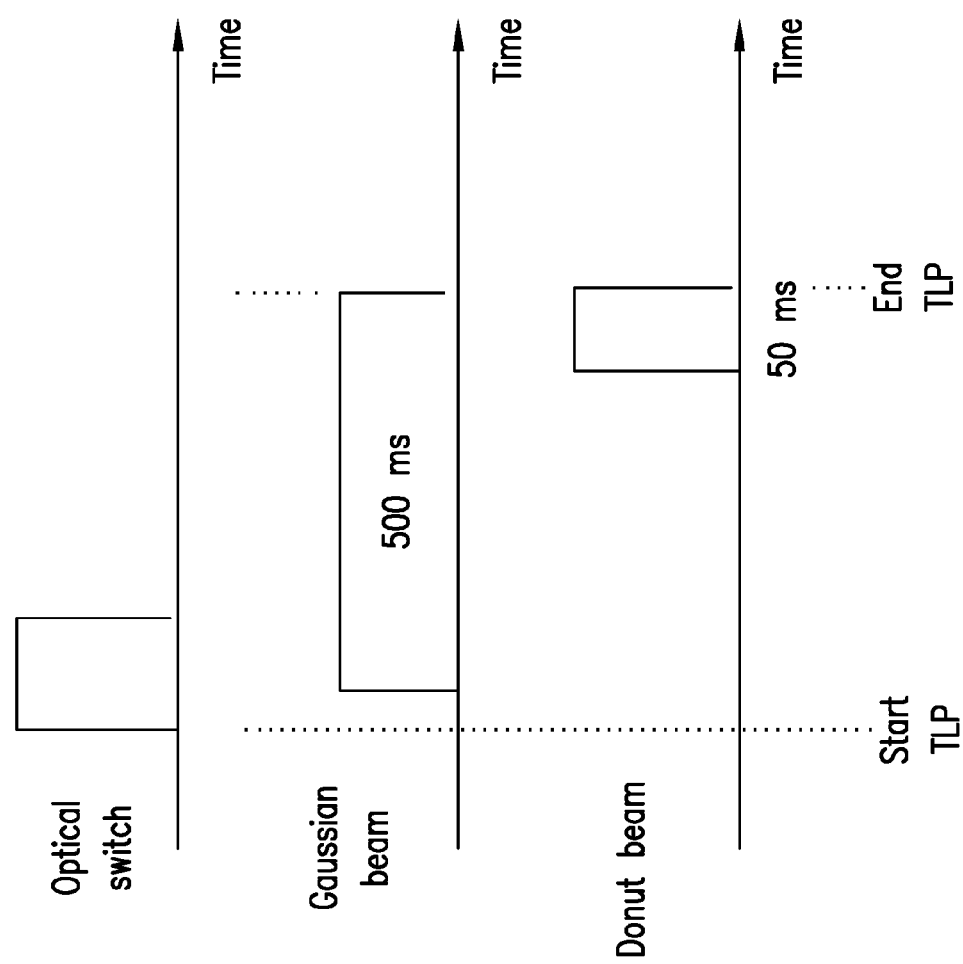
FIG. 6 is a timing diagram for dual pulse treatment, according to an embodiment of the present invention.

A third illumination strategy can be a combination of both those described above. A short pulse width donut beam can be superimposed on a long pulse width Gaussian beam toward the end of the short pulse width donut beam's duration, as indicated by the timing diagram in FIG. 6. This strategy allows the hair shaft's 407 temperature to be elevated by the extended TLP directed at the hair shaft 407, followed by the donut shaped pulse just prior to the termination of the Gaussian pulse. The Gaussian pulse may have a pulsed width in the range of 100 to 500 ms, while the donut shaped pulse width is between 5 and 50 ms. In principle, the two laser diodes 701 and 702 may have different wavelength and deliver different fluence levels, which could be matched for the hair color.

Figure 7:
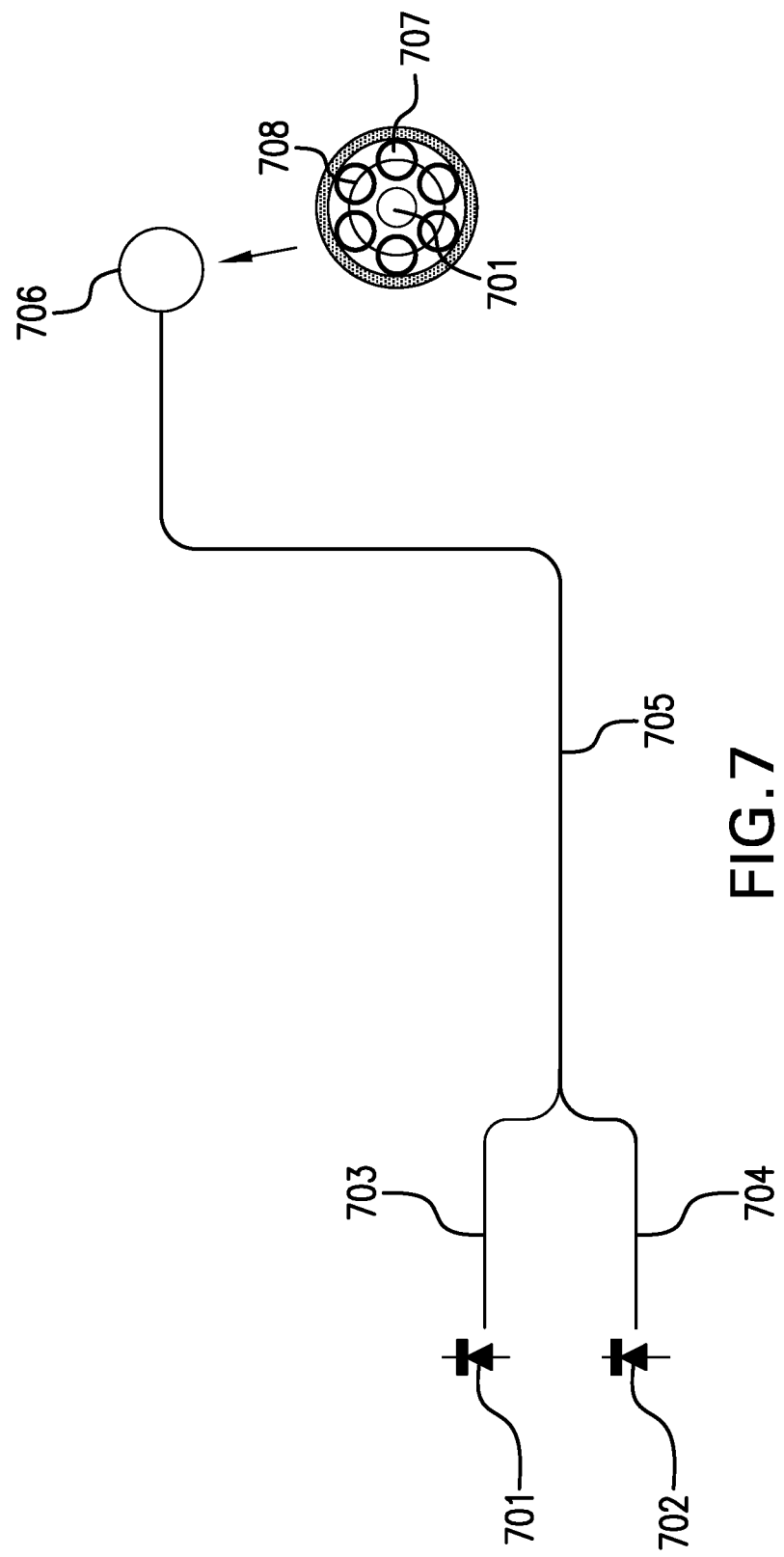
FIG. 7 is a schematic of a dual laser diode illumination scheme, according to an embodiment of the present invention.

Referring to FIG. 7, Laser Diode (LD1) 701 is pigtailed to a single multimode fiber 703 which forms a central part of the distal end 706 of a fiber optic assembly 705. Laser Diode (LD2) is pigtailed to plurality of multimode fibers 704 which are arranged in an annular pattern 707 surrounding the single multimode fiber 703. In this way, LDs 701 and 702 may either have identical or dissimilar spectral and power properties. The distal end 706 can be integrated with the source aspheric imaging lens assembly 129 illustrated by FIG. 1.

There may be instances when a larger spot is required. As discussed above, with reference to FIGS. 2A and 2B, it is possible to produce any arbitrary illumination shape. For example, an elliptical spot which increases the spot dimension along one axis, while keeping the area small could be used. However, there may be instances when this approach is also not adequate. In such situations a large treatment area can be synthesized by scanning the small spot over the target area. U.S. Pat. No. 7,101,365 to Sharon, the disclosure of which is incorporated herein by reference, describes a manual means to pivot an entire hand piece to obtain a limited scan. While Altshuler (discussed above) and U.S. Pat. No. 5,860,967 to Zavisian, the disclosure of which is incorporated herein by reference, include a 2-D scanning mechanism in the hand piece. Embodiments of the present invention achieve desired scanning of the target 106 by scanning an image of the source at the proximal end 110 of the CIF 108.

Referring to FIG. 8A, dots 801 and 802 show two arbitrary positions of the TLP on the treatment area 103. FIG. 8B illustrates positions of the corresponding dots 801 and 802 on the proximal end 110 of the CIF 108. A target scan path corresponds to a scanned source image on the proximal end 110.

The scanned image can be generated in number of ways. FIG. 8C illustrates a 2-D mechanical scanner using mirrors 803 and 804. A laser source beam 805 bounces off the mirrors 803 and 804 to define a scan path 806. FIG. 8D illustrates an alternative means of obtaining the source scan, using a 1×N fiber optic switch. In other words, output of an input fiber 807 can be directed to any one of output fibers 808 by means of, for example, a rotating concave mirror 809. Other types of switches may be used. The output fibers 808 form the distal end 706 of the fiber optic bundle 705 described in FIG. 7. An important difference between the Sharon and Altshuler schemes is that all scanning components are in the electronic console 102, none of the scanning components are in the HPA 100. This ensures a compact and safe hand piece suitable for non-medical facilities.

There are certain situations when indiscriminate hair removal using a large diameter spot is not desirable. As an example, for cosmetic purposes, patients may require an alteration of the hair density in certain parts of the human anatomy rather than total hair removal. For such applications a LHR system must be capable of targeting individual hair follicles. The HPA 100 described above can be used on a robotic platform to remove hair from any random location. One such embodiment includes a 3-D vision system capable of creating a digital map of a surface to be treated. Appropriate software algorithms that analyze hair distribution and hair angle determine optimum location information of hair follicles to receive laser treatment. The location information drives the robotic arm to automatically complete the treatment. Safety features, built around limit switches, ensure that the high energy spot remains within the treatment area.

Another preferred embodiment of the HPA 100 is illustrated by FIG. 9. The CIF 108 is surrounded by a plurality of multimode fibers 901 which are used for delivering high energy optical pulses to the hair follicle. Output of the multimode fibers 901 is combined into a single spot at an entrance to the target 106. A radially bi-focal lens 902 provides disparate magnifications for the CIF 109 and the multimode fibers 901. The multimode fibers 901 can be used to increase the target fluence by using a plurality of optical sources at the same emission wavelength, or alternatively, sources with output at different wavelengths could be combined to enhance efficacy of the treatment.

An example of a fluence calculation in a preferred embodiment is as follows. An expected fluence $F_t$ [J·cm$^{-2}$] at the target 106 of area $A_t$ [cm$^2$] to the power $P_f$ emanating from a pigtailed laser diode assembly 129 is given by Equation (1):

$$F_t = \eta \frac{P_f \sigma_T}{A_T} \tag{1}$$

where $\eta$ represents all the transmission losses from the output of the fiber assembly 129 to the laser spot illuminating the treatment area 106 and $\sigma_T$ is the pulse width or duration of the optical energy pulse which can be easily controlled between 100 µs to 1 s. Using a conservative estimate of $\eta=0.85$, $P_f=200$ mW, $A_t=10^{-4}$ cm$^2$, which is a typical diameter of the hair shaft, and $\sigma_T=50$ ms, $F_t=85$ J·cm$^2$ is obtained. Thus, the fluence can be controlled through a combination of parameters, $P_f$, $\sigma_T$, and $A_T$.

While the invention has been shown and described with reference to certain embodiments of the present invention thereof, it will be understood by those skilled in the art that various changes in from and details may be made therein without departing from the spirit and scope of the present invention as defined by the appended claims and equivalent thereof.

What is claimed is:

1. A portable device comprising:
    a coherent imaging fiber;
    an optical switch;
    a plurality of multimode optical fibers; and
    an imaging microlens assembly,
    wherein the coherent imaging fiber transports an image of a targeted hair follicle for viewing by a user of the portable device, and
    wherein the coherent imaging fiber delivers laser energy to the targeted hair follicle.

2. The portable device of claim 1, wherein cellular structures of the targeted hair follicle are damaged by elevated temperature photo-induced by the laser energy.

3. The portable device of claim 1, wherein the coherent imaging fiber includes an outer ring comprising the plurality of multimode optical fibers for illumination of the targeted hair follicle.

4. The portable device of claim 1, wherein the optical switch modulates an optical signal to define ON/OFF states of the portable device.

5. The portable device of claim 1, further comprising a radially bi-focal lens providing disparate magnifications for the coherent imaging fiber and the plurality of multimode optical fibers.

* * * * *